United States Patent [19]

Spearmon et al.

[11] Patent Number: 4,861,593
[45] Date of Patent: Aug. 29, 1989

[54] CONDITIONER-HAIR DRESSING

[76] Inventors: JoAnn M. Spearmon, 4616 21st St., Mount Ranier, Md. 20712; Sharon I. Jackson, 2604 Pinebrook, Landover, Md. 20785

[21] Appl. No.: 114,058

[22] Filed: Oct. 29, 1987

[51] Int. Cl.$^4$ .............................................. A61K 7/075
[52] U.S. Cl. ................................... 424/195.1; 424/74; 514/552; 514/880; 514/881
[58] Field of Search ............... 424/195.1, 74; 514/552, 514/880, 881

[56] References Cited

U.S. PATENT DOCUMENTS

| | | | |
|---|---|---|---|
| 4,088,751 | 5/1978 | Kenkare et al. | 424/65 |
| 4,201,235 | 5/1980 | Ciavatta | 424/47 |
| 4,551,330 | 11/1985 | Wagman et al. | 424/66 |
| 4,603,046 | 7/1986 | Georgalas et al. | 424/60 |

Primary Examiner—William R. Dixon, Jr.
Assistant Examiner—Ellen M. McAvoy
Attorney, Agent, or Firm—Jerome J. Norris

[57] ABSTRACT

A creamy water-in-oil conditioner-dressing for hair comprising: wheat germ oil, Brewers yeast flakes, the oils of vitamins A, D and E, propylene glycol, glycerol, jojoba oil, methyl and propyl parabens, deionized water, petrolatum, Sodium Lauryl Sulfate, n-stearyl alcohol, n-cetyl alcohol and fragrance.

2 Claims, No Drawings

CONDITIONER-HAIR DRESSING

BACKGROUND OF THE INVENTION

The present invention pertains to water-in-oil emulsion compositions which serve as both a conditioner and a dressing for topical application to the hair. The formulation is characterized by a creamy non-greasy appearance, and is stable against separation at ambient temperatures.

FIELD OF THE INVENTION

It is well known that after the hair and scalp are washed, it is often times common practice to use a conditioner in order to untangle the hair and provide the hair with protection against the drying effects of the environment as a result of the conditioner's adherence capabilities. Thereafter a grooming agent is added to the conditioned hair in order to provide luster, maintain it in a certain style and prevent it from 'drying out' and becoming brittle from the loss of too much moisture.

A problem of no small dimensions in the area of grooming is the fact that oil based grooming compositions have not been fully satisfactory because of problems of uneven spreading, a greasy appearance, and greasiness to the touch. For these reasons, oil-based grooming compositions have been increasingly replaced by synthetic polymers which adhere to the hair, lack the greasy appearance and also facilitates the untangling of wet hair. Included amongst these polymers are polyamines, polyaminoamides and quaternary polyammonium compounds.

However, despite the mentioned beneficial characteristics of these synthetic polymers, they nevertheless leave much to be desired insofar as lending luster, glow and natural softness to the hair. Therefore, while these synthetic polymers function well for purposes of conditioning the hair subsequent to cleansing, they are not ideally suitable for grooming the hair and leaving it with glow, luster and natural softness to the touch.

The class of synthetic polymers referred to have been termed cationic polymers, and efforts have been made to admix these polymers in oils in an attempt to combine their functional conditioning properties with the grooming properties of said oils; however, these attempts have not been possible because, in many cases the polymers of interest were not isolatable in the dry state and only available in aqueous solutions in which the polymers were not soluble in oils. In other cases, these polymers were soluble in oils but their conditioning properties were either lost or severely inhibited.

It is an objective of the present invention to provide a water-in-oil emulsion composition which serves as both a conditioner and a dressing for the hair.

A further objective of the invention is to provide a conditioner-dressing composition for hair in which the dressing oils utilized therein are combined with other components in a manner so as to avoid uneven oil spreading on the hair, the greasy appearance associated with uneven oil spreading, and the greasy sensation to the touch upon feeling hair having oil unevenly spread thereon.

A yet further objective of the invention is to provide a conditioner-dressing composition for the hair which utilizes a method of combining natural vegetable oils with a mixture containing cetyl alcohol and petrolatum, and further processing the admixture of natural vegetable oils, cetyl alcohol petrolatum by incorporating vitamin oils, polyhydric alcohols and brewers yeast flakes to produce a creamy water in oil emulsion composition that is stable against separation of the oils at ambient temperatures.

SUMMARY OF THE INVENTION

The conditioner-hair dressing composition of the invention is essentially obtained by: (A) admixing cetyl alcohol and petrolatum at elevated temperatures and allowing the admixture to cool to ambient or normal room temperature; (B) adding natural vegetable oils and vitamin oils to said admixture; (C) mixing the combination of (A) and (B) to provide a homogeneous blend; (D) adding one-half quantity of de-ionized water; (E) adding a mixture composed of cetyl alcohol, stearyl alcohol, white petrolatum, glycerol, sodium lauryl sulfate and propyl paraben and mixing to form a homogeneous blend; (F) adding propylene glycol and mixing; (G) pulverizing methyl paraben and propyl paraben, adding glycerol thereto with stirring until said parabens are dissolved; and adding the solution to (F) with mixing; (H) pulverizing Brewers yeast flakes in deionized water until said flakes are dissolved and adding the solution of said dissolved flakes in three parts to (F) with thorough mixing; and adding fragrance.

The conditioner-hair dressing composition prepared by the invention process is a homogeneous water-in-oil emulsion characterized by a creamy appearance and feel. It functions as a conditioner for the hair and scalp and helps retain natural moisture in the hair. As a conditioner, it also helps to detangle the hair and protect the hair from breakage. However, despite the efficacy of the composition as a conditioner, the admixture does not inhibit the oil phase from functioning as a dressing or grooming material because of any uneven spreadability characteristic of the oil in the mixture. As a result, the oil is evenly spreadable to fully soften and moisturize the hair as well as provide luster to it.

DETAILED DESCRIPTION OF THE INVENTION

In accordance with the invention, it has been found that oil based hair grooming compositions in which the oils are vegetable oils can be satisfactorily blended with higher alcohols such as n-cetyl and n-stearyl alcohol to formulate a creamy water-in-oil emulsion in which the hair grooming and dressing characteristics of the oils are kept intact and the conditioning qualities of the balance of the compositions are also preserved intact.

The method of formulating the conditioner-hair dressing composition is illustrated in the following preparation:

EXAMPLE I 90 ml of deionized water is placed in the bottom of a double boiler and heater for about 5 to 7 minutes to bring the water to a temperature of 212 degrees Fahrenheit. About 25 grams of n-cetyl alcohol is pulverized in a dish heated by steam and 120 grams of white petrolatum is added to the alcohol in said dish and the two materials are allowed to melt completely, in about 5 minutes. The melted mixture is then poured into a mixing bowl and the mixture is stirred vigorously for about 1 minute to insure that all of the alcohol has melted completely. The mixture is allowed to cool for about 1 minute to ambient or surrounding room temperature of about 67 degrees Fahrenheit.

30 ml of jojoba oil, 30 ml of wheat germ oil, 24 ml of one-half vitamin A oil and one-half vitamin D oil and 12 ml of vitamin E oil are added sequentially in the stated order to the cooled mixture, and the entire admixture is blended for 5 minutes or longer until a uniform blend is obtained.

108 ml of deionized water is then added.

Next, a combined mixture capable of absorbing 30% of its weight in water, and composed of:

15 grams: n-cetyl alcohol
18.9 grams: glycerol
14.7 grams: white petrolatum
0.1 grams: propyl paraben
0.2 grams: sodium lauryl sulfate, and
11.1 grams: n-stearyl alcohol is added to the uniform blend and the combined admixture is thoroughly mixed to obtain a homogeneous mixture.

36 ml of propylene glycol is added to the mixture, and the propylene glycol modified mixture is mixed thoroughly for at least 3 minutes to provide homogeneity throughout the mixture.

0.2 gram of propyl paraben and 0.2 gram of methyl paraben are pulverized in a mortar and 30.0 grams of glycerol is added thereto and stirred in thoroughly until the parabens are completely dissolved. The glycerol dissolved parabens are added to propylene glycerol modified admixture and the combined mixture is thoroughly mixed until homogeniety is reached.

0.3 grams of Brewers yeast flakes are added to 108 ml of deionized water and stirring is performed until the flakes are dissolved whereupon the separate parts are added to the already formed mixture, and thorough mixing is performed after each addition until a homogeneous mixture is formed. 10 ml of fragrance is then added and the fragrance modified mixture is thoroughly mixed until a homogeneous water-in-oil emulsion having a creamy appearance and creamy touch is obtained.

The composition was applied to the hair after it had been washed and towel dried and the hair untangled with ease upon combing because the hair remained substantially softened and highly moist after towel drying and this established that the non-vegetable oil components of the cream functioned as an excellent conditioner. However, the vegetable oil component of the water-in-oil emulsion provided luster to the hair and allowed the hair to have a non-greasy look and non-greasy feel to the touch, and thus confirmed that the vegetable oil component was spread evenly over the hair, and therefore functioned as a good dressing or grooming material in the creamy composition.

EXAMPLE II

Same as Example I, except that ethanol was used in place of cetyl alcohol and n-propanol was used in place of stearyl alcohol. In this case, the creamy water-in-oil emulsion did not result, and the hair was left with a greasy dull appearance without luster when the composition was applied to the hair after washing and towel drying. Moreover, the hair did not untangle easily and there was more hair breaking upon pulling a comb through the hair than in the case of Example I.

EXAMPLE III

Same as Example I, except that ethanol was used in the place of propylene glycol and n-propanol was used in the place of glycerol.

In this case, the creamy water-in-oil emulsion did not result, and the hair was left with a greasy dull appearance without luster, and was greasy to the touch when the composition was applied to the hair after washing and towel drying. Moreover, the hair was not as moist after application of this composition, and the hair breaking was greater than that in Example I, upon pulling a comb through the hair.

The preferred embodiments of the invention, the water-inoil creamy emulsion will be composed of the following formulation:

Wheat Germ Oil: 30 ml
Brewers Yeast Flakes: 0.3 gm
Vitamin E Oil: 12 ml
Vitamin A Oil: 12 ml
Vitamin D Oil: 12 ml
Propylene Glycol: 36 ml
Glycerol: 30 ml
Jojoba Oil: 30 ml
Methyl Paraben: 0.2 gm
Propyl Paraben: 0.2 gm
Deionized Water: 216 ml
Petrolatum: 120 gm
Sodium Lauryl Sulfate: 0.2 gm
N-Stearyl Alcohol: 11.1 gm
N-Cetyl Alcohol: 25 gm
Fragrance: 10 ml It has been found that if the mixing sequence for preparing the water-in-oil emulsion is not observed, the oil phase of the final product will separate out. When such a separation occurs, the conditioner-dressing benefits described in Example I are not realized.

It is to be understood that various changes may be made in the invention composition and process described, without affecting the improved conditioning and grooming results obtained. Thus, variations in conditions as to times, temperatures and amounts of ingredients used at different junctures of the process can be made without departing from the scope of the invention, which has been set forth in an illustrative but non-limiting manner.

What is claimed is:

1. A creamy homogeneous water-in-oil hair conditioner-hair dressing composition for topical application to the hair consisting essentially of:
Wheat Germ Oil: 30 ml
Brewers Yeast Flakes: 0.3 gm
Vitamin E Oil: 12 ml
Vitamin A Oil: 12 ml
Vitamin D Oil: 12 ml
Propylene Glycol: 36 ml
Glycerol: 30 ml
Jojoba Oil: 30 ml
Methyl Paraben: 0.2 gm
Propyl Paraben: 0.2 gm
Deionized Water: 216 ml
Petrolatum: 120 gm
Sodium Lauryl Sulfate: 0.2 gm
n-Stearyl Alcohol: 11.1 gm
n-Cetyl Alcohol: 25 gm
Fragrance: 10 ml 2. A method of preparing a creamy homogeneous water-in-oil hair conditioner-hair dressing for topical application to the hair, comprising:
   (a) melting about 25 grams of n-cetyl alcohol in about 120 grams of petrolatum and allowing the melt to cool;
   (b) adding sequentially to said melt, about 30 ml of jojoba oil, about 30 ml of wheat germ oil, a mixture of about 12 ml each of vitamin A oil, vitamin D oil and vitamin E oil and blending the until a uniform admixture is obtained;
(c) adding about 108 ml of deionized water;
(d) adding a combined mixture of about:
- 15 gms: n-Cetyl Alcohol
- cm 18.9 gms: Glycerol
- 14.9 gms: White Petrolatum
- 0.1 gms: Propyl Paraben
- 0.2 gms: Sodium Lauryl Sulfate
- 11.1 gms: n-Stearyl Alcohol (e) blending to obtain a homogenous mixture;
(f) adding about 36 ml of proplylene glycol and blending until homogeneity is obtained;
(g) pulverizing a mixture of about 0.2 gms of methyl paraben and about 0.2 gms of propyl paraben and adding about 30.0 gms of glycerol with stirring until the parabens are dissolved;
(h) adding the dissolved mixture from step g) to the mixture from step f) and blending to homogeneity;
(i) adding about 0.3 gms of Brewers yeast flakes to about 108 ml of deionized water, and stirring until the flakes are dissolved;
(j) adding the dissolved material from step i) to the material of step h) in three separate portions while stirring, and continuing to stir until a homogeneous mixture is formed; and
(k) adding about 10 ml of fragrance to the product of step j) while mixing to form a creamy water-in-oil emulsion.

* * * * *